(12) United States Patent
Radmall et al.

(10) Patent No.: US 9,402,696 B2
(45) Date of Patent: Aug. 2, 2016

(54) PIN CONNECTOR FOR ORTHODONTIC FORCE MODULE

(71) Applicant: Ultradent Products, Inc., South Jordan, UT (US)

(72) Inventors: Colby M. Radmall, Lehi, UT (US); Robert A. Miller, Culpeper, VA (US)

(73) Assignee: Ultradent Products, Inc., South Jordan, UT (US)

( * ) Notice: Subject to any disclaimer, the term of this patent is extended or adjusted under 35 U.S.C. 154(b) by 98 days.

(21) Appl. No.: 14/209,644

(22) Filed: Mar. 13, 2014

(65) Prior Publication Data

US 2014/0272755 A1  Sep. 18, 2014

Related U.S. Application Data

(60) Provisional application No. 61/785,153, filed on Mar. 14, 2013.

(51) Int. Cl.
| | |
|---|---|
| A61C 3/00 | (2006.01) |
| A61C 7/34 | (2006.01) |
| A61C 7/28 | (2006.01) |
| A61C 7/00 | (2006.01) |
| A61C 7/36 | (2006.01) |

(52) U.S. Cl.
CPC ... *A61C 7/34* (2013.01); *A61C 7/00* (2013.01); *A61C 7/282* (2013.01); *A61C 7/36* (2013.01)

(58) Field of Classification Search
CPC ............ A61C 7/34; A61C 7/00; A61C 7/282; A61C 7/36
USPC .......................................... 433/18, 19, 21, 14
See application file for complete search history.

(56) References Cited

U.S. PATENT DOCUMENTS

| | | | |
|---|---|---|---|
| 5,718,576 A | 2/1998 | Schnaitter et al. | |
| 5,829,975 A * | 11/1998 | Gold | A61C 7/36 433/19 |
| 6,234,791 B1 * | 5/2001 | Cleary | A61C 7/00 433/18 |

* cited by examiner

*Primary Examiner* — Cris L Rodriguez
*Assistant Examiner* — Mirayda A Aponte
(74) *Attorney, Agent, or Firm* — Workman Nydegger (57) ABSTRACT

A pin connector for attaching an orthodontic force module to an orthodontic appliance is configured to preferentially bend in a middle segment along an elongate pin body of the pin connector. The pin connector includes an elongate pin body and an extension rod extending laterally from an end of the pin body for interconnecting the pin body and an orthodontic force module. The elongate pin body includes first, second and third segments, with the second segment having reduced cross-sectional diameter relative to the first and third segments so that pin body preferentially bends in the second segment rather than the first and third segments when attaching the orthodontic force module to the orthodontic appliance. This provides a preselected amount of distance or play between the orthodontic force module and the orthodontic appliance.

27 Claims, 6 Drawing Sheets

PIN CONNECTOR FOR ORTHODONTIC FORCE MODULE

CROSS REFERENCE TO RELATED APPLICATION

This Application claims the benefit of U.S. Provisional Application No. 61/785,153, filed Mar. 14, 2013, the disclosure of which is incorporated herein in its entirety.

BACKGROUND OF THE INVENTION

1. The Field of the Invention

The present invention is in the field of orthodontics, more particularly in the field of devices for correction of class II and/or class III malocclusions.

2. The Relevant Technology

Orthodontics is a specialized field of dentistry that involves the application of mechanical forces to urge poorly positioned or crooked teeth into correct alignment and orientation. Orthodontic procedures can be used for cosmetic enhancement of teeth, as well as medically necessary movement of teeth to correct overjets and/or overbites. For example, orthodontic treatment can improve the patient's occlusion, or enhanced spatial matching, of corresponding upper and lower teeth.

Orthodontic treatment of some patients includes correction of the alignment of the upper dental arch relative to the lower dental arch. Certain patients have a condition referred to as a Class II malocclusion, which is a condition involving the posterior relationship of the mandible to the maxillae and in which the mesiobuccal cusp of the permanent maxillary first molar occludes mesial to the buccal groove of the permanent mandibular first molar (also known as retrognathia, or overjet). Other patients may have an opposite condition referred to as a Class III malocclusion wherein the lower dental arch is located forward of the upper dental arch when the jaws are closed (prognathia, or negative overjet).

Class II and Class III malocclusions may be corrected with the use of a force-applying system such as headgear, elastic, or an intraoral force module. Headgear is generally disfavored because it is bulky and often a source of embarrassment for the patient. Intraoral force modules have gained increasing acceptance as they can remain fixed in place over the course of treatment so as to typically not be removable by the patient, and are less aesthetically objectionable compared to traditional headgear.

Examples of intraoral force modules are disclosed in PCT Publication No. WO 2012/018648 and U.S. Pat. Nos. 5,828,875; 5,738,514; 5,711,667; 5,562,445; 6,358,046; 6,162,051; 5,964,588; and 5,944,518, the disclosures of which are incorporated herein by reference. Intraoral force modules can be attached to an orthodontic buccal tube or other orthodontic appliance attached to a patient's tooth using a bendable pin, which can require a high level of skill and/or trial and error to provide the correct distance or amount of play between the force modules and orthodontic appliance.

SUMMARY OF THE INVENTION

Disclosed herein are pin connectors for attaching an orthodontic force module to an orthodontic buccal tube or other orthodontic appliance and which are configured to bend in a predetermined region. Also disclosed are orthodontic force module assemblies that incorporate a pin connector configured to bend in a predetermined region, as well as methods for attaching orthodontic force module assemblies to an orthodontic buccal tube or other orthodontic appliance.

Example pin connectors include an elongate pin body having a region of reduced cross-sectional diameter compared to a cross-sectional diameter of at least one adjacent region. The region of reduced cross-sectional diameter causes the elongate pin body to preferentially bend in the region of reduced cross-sectional diameter when attaching the pin connector to an orthodontic buccal tube or other orthodontic appliance. Pin connectors may also include an extension rod extending laterally form an end of the pin body and configured for attachment to an orthodontic force module. The elongate pin body and extension rod can be integrally formed as a single piece of material.

According to one embodiment, the elongate pin body includes a plurality of segments. A first pin body segment extends from the proximal end of the pin body to a first location on the pin body between the proximal and distal ends. A second pin body segment extends distally from the first pin body segment to a second location on the pin body between the first location and the distal end. A third pin body segment extends distally from the second pin body segment to the distal end of the pin body. The second pin body segment provides the region of reduced cross-sectional diameter.

The pin connector can include an elongate pin body with a length and a region of reduced cross-sectional diameter positioned along the elongate pin body in order for the pin connector to provide a predetermined play between the force module and orthodontic buccal tube or other orthodontic appliance when attached thereto. The predetermined play can be in a range of about 1.5 mm to about 2.5 mm.

According to another embodiment, an orthodontic force module assembly for correcting Class II and/or Class III malocclusions comprises an orthodontic force module and a pin connector as disclosed herein at a distal end of the force module for attachment of the force module to an orthodontic buccal tube or other orthodontic appliance. The orthodontic force module assembly may further include attachment structure (e.g., a hook or recess) at the proximal end of the orthodontic force module assembly for attachment to an arch wire and/or a bracket.

According to another embodiment, a method of attaching an orthodontic force module to an orthodontic buccal tube or other orthodontic appliance comprises: (1) providing an orthodontic force module with a pin connector at an end thereof; (2) inserting an elongate pin body of the pin connector into a tunnel of the orthodontic buccal tube or other orthodontic appliance; and (3) bending a portion of the elongate pin body in order to secure the pin connector to the orthodontic buccal tube or other orthodontic appliance, (4) the elongate pin body preferentially bending in a predetermined region as a result of the predetermined region having a reduced cross-sectional diameter compared to a cross-sectional diameter of at least one adjacent region.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. The drawings depict only typical embodiments of the invention and are not therefore to be considered limiting of its scope.

DETAILED DESCRIPTION OF THE PREFERRED EMBODIMENTS

Disclosed herein are improved pin connectors for use in attaching an orthodontic force module to an orthodontic buccal tube or other orthodontic appliance. The improved pin connectors are configured to bend in a predetermined region in order to provide a desired distance or play between the orthodontic force module and the orthodontic buccal tube or other orthodontic appliance. Also disclosed are improved methods for attaching an orthodontic force module to an orthodontic buccal tube or other orthodontic appliance that reduces or eliminates the need to mark the pin connector or otherwise rely on a visual determination of the proper bending location. In this way the improved pin connectors and methods of orthodontic force module to an orthodontic buccal tube or other orthodontic appliance simplify the installation procedure and reduce or eliminate bending error. Reducing or eliminating repeat pin bending procedures is beneficial for both the orthodontic practitioner and the patient.

Figure 1A:
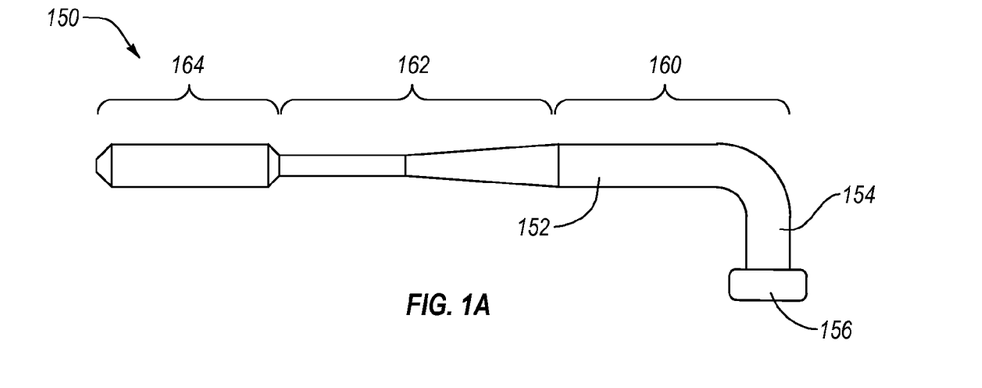
FIG. 1A illustrates an example pin connector for attaching an orthodontic force module to an orthodontic appliance and that is configured to preferentially bend in a predetermined region.
Figure 1B:
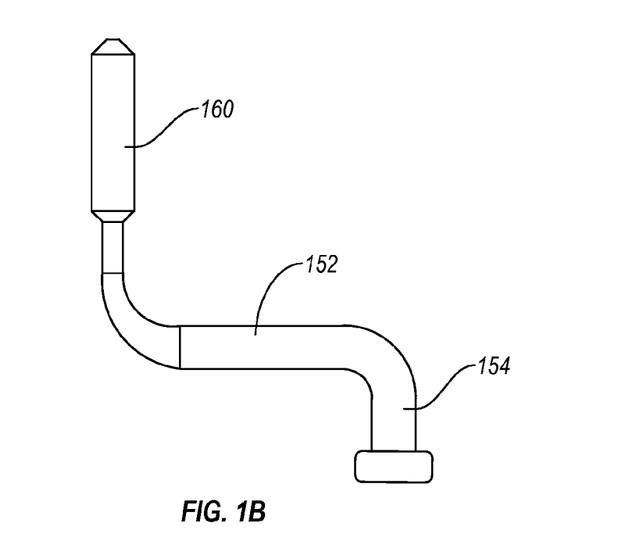
FIG. 1B illustrates the pin connector of FIG. 1A, showing the elongate pin body bent across the first 90° of a 180° bend.
Figure 1C:
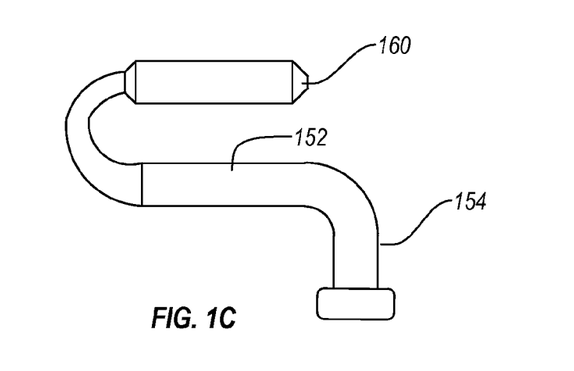
FIG. 1C illustrates the pin connector of FIG. 1B, showing progression of the bend when the bend reaches 180°.

Referring now to the drawings, FIGS. 1A-1C illustrate an example pin connector 150 for use in attaching an orthodontic force module to an orthodontic buccal tube or other orthodontic appliance and configured to bend in a predetermined region. Pin connector 150 includes an elongate pin body 152 extending between a proximal end and a distal end and an extension rod 154 rigidly attached to and extending laterally form the proximal end of pin body 152 and including a flange or protrusion 156 for attachment to an end of an orthodontic force module (i.e, means for attaching pin connector 150 to an end of an orthodontic force module). To provide a region of reduced cross-sectional diameter for preferential bending when attaching pin connector 150 to an orthodontic buccal tube or other orthodontic appliance, pin body 152 includes or is divided into a plurality of segments, including: a first pin body segment 160 extending from the proximal end of pin body 152 to a first location on pin body 152 between the proximal and distal ends; a second pin body segment 162 extending distally from first pin body segment 160 to a second location on pin body 152 between the first location and the distal end; and a third pin body segment 164 extending distally from second pin body segment 162 to the distal end of pin body 162. Second pin body segment 162 is configured to provide the region of reduced cross-sectional diameter, which is less than the cross-sectional diameters of first and third segments 160, 164.

FIGS. 1B and 1C illustrate how the region of reduced cross-sectional diameter provided by second pin body segment 162 can cause elongate pin body 152 to preferentially bend in the region of second pin body segment 162 rather than in first and third body segments 160, 164. The total illustrated bend is 180°, which permits pin connector 150 to securely attach an orthodontic force module to a buccal tube or other orthodontic appliance. FIG. 1B provides an example illustration of how elongate pin body 152 can first bend across the first 90° of the 180° bend. More particularly, depending on the relative cross-sectional diameters of first and second pin body segments 160, 162, the bend can begin at or near the interface between first and second pin body segments 160, 162 and continue along the length of second pin body segment 162 in a controlled manner. FIG. 1C illustrates how the bend can continue progressing along the length of second pin body segment 162 so as to end at or near the interface between second and third pin body segments 162, 164 when the bend reaches 180°.

Figure 2A:
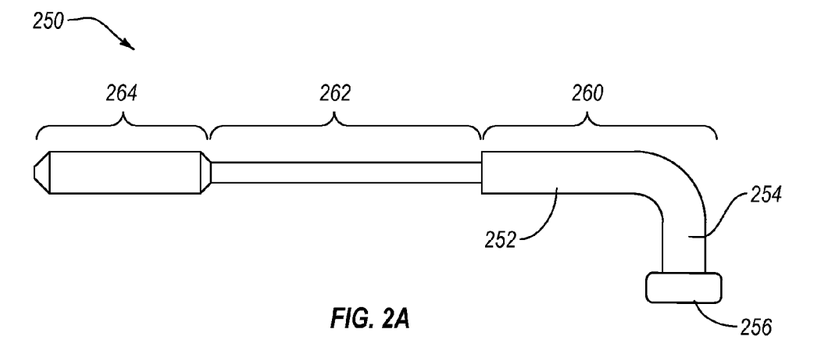
FIG. 2A illustrates another example pin connector for attaching an orthodontic force module to an orthodontic appliance and that is configured to preferentially bend in a predetermined region.
Figure 2B:
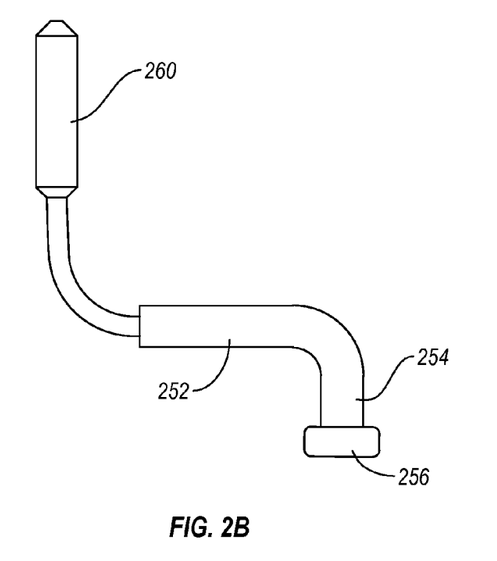
FIG. 2B illustrates the pin connector of FIG. 2A, showing the elongate pin body bent across the first 90° of a bend.
Figure 2C:
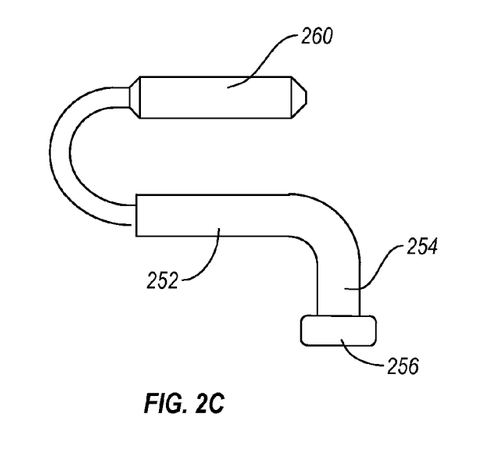
FIG. 2C illustrates the pin connector of FIG. 2B, showing progression of the bend when the bend reaches 180°.

FIGS. 2A-2C illustrate an alternative embodiment of an example pin connector 250 configured to bend in a predetermined region. Pin connector 250 is similar to pin connector 150 illustrated in FIGS. 1A-1C except that region of reduced cross-sectional diameter in pin connector 250 has a more continuous cross-sectional diameter. It is posited that providing a gradually reducing cross-sectional diameter can, in some cases, provide a more controlled bend along the length of the region of reduced diameter compared to a region of reduced diameter having a constant cross-sectional diameter.

As illustrated in FIG. 2A, pin connector 250 includes an elongate pin body 252 extending between a proximal end and a distal end and an extension rod 254 rigidly attached to and extending laterally form the proximal end of pin body 252. A flange or protrusion 256 provides means for attaching pin connector 250 to an end of an orthodontic force module. Pin body 252 includes a first pin body segment 260 extending from the proximal end of pin body 252 to a first location on pin body 252 between the proximal and distal ends; a second pin body segment 262 extending distally from first pin body segment 260 to a second location on pin body 252 between the first location and the distal end; and a third pin body segment 264 extending distally from second pin body segment 262 to the distal end of pin body 262. The cross-section diameter of second pin body segment 262 is less than the cross-sectional diameters of first and third segments 260, 264.

FIGS. 2B and 2C illustrate how the region of reduced cross-sectional diameter provided by second pin body segment 262 can cause elongate pin body 252 to preferentially bend in the region of second pin body segment 262 rather than in first and third body segments 260, 264. FIG. 2B illustrates how pin body 152 can begin bending during the first 90° of the bend at or near the interface between first and second pin body segments 260, 262. FIG. 2C illustrates how the bend can progress along the length of second pin body segment 262 so as to end at or near the interface between second and third pin body segments 262, 264 when the bend reaches 180°.

Figure 3A:
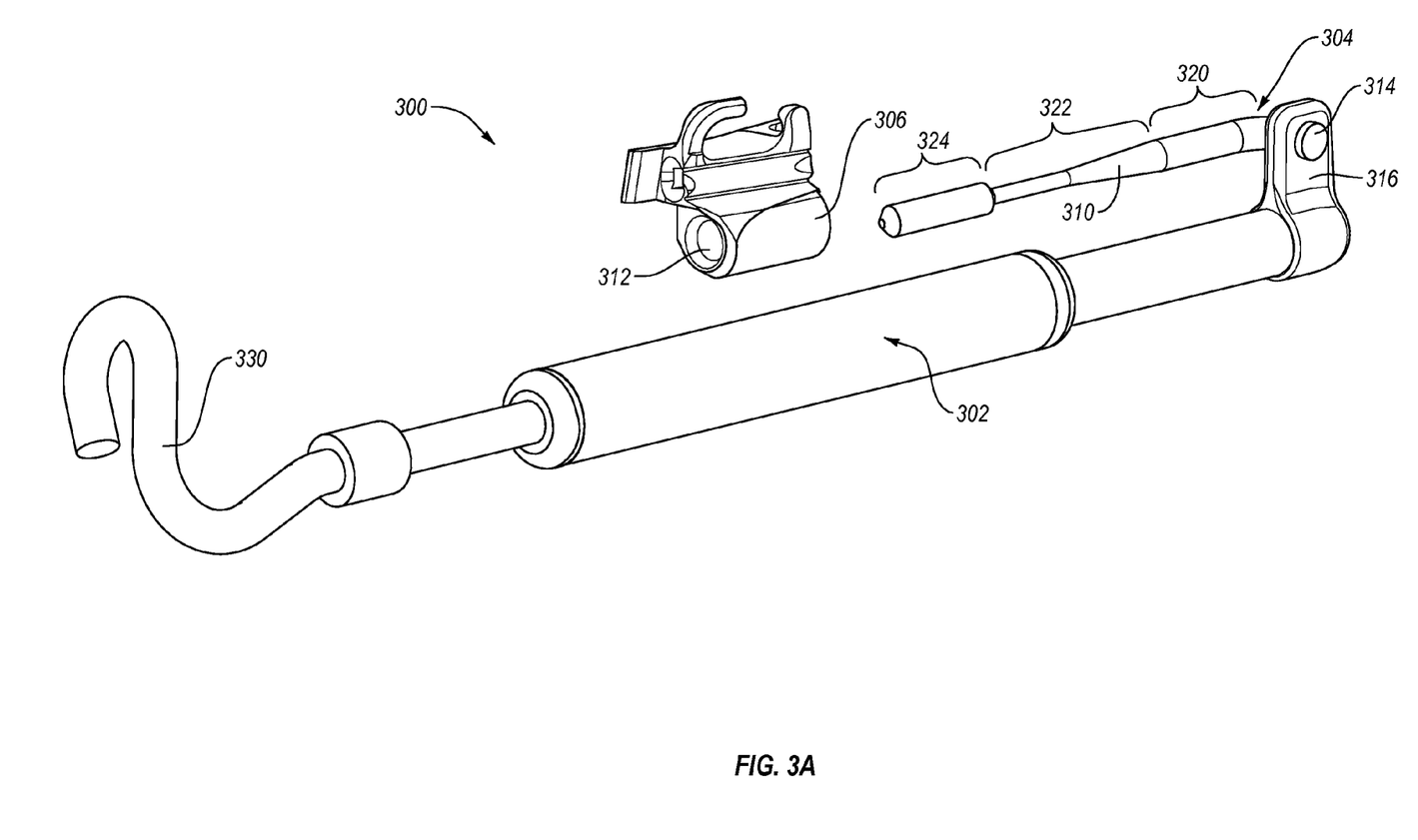
FIG. 3A illustrates a pin connector being used to attach an orthodontic force module to an orthodontic buccal tube, showing the orthodontic force module before attachment to the buccal tube.
Figure 3B:
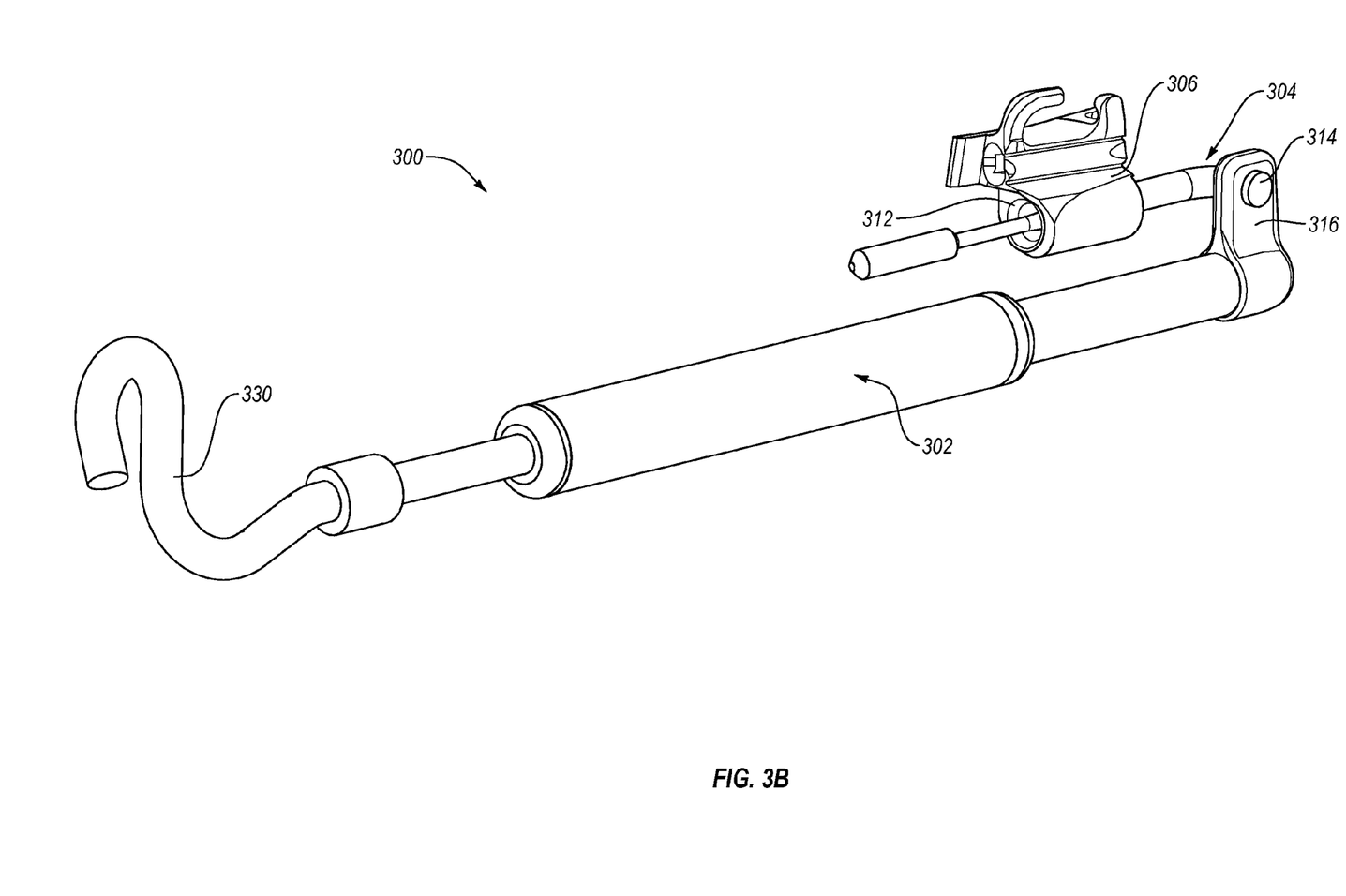
FIG. 3B illustrates a pin connector being used to attach an orthodontic force module to an orthodontic buccal tube as in FIG. 3A, showing a pin body of the pin connector inserted through a tunnel of the buccal tube.

FIGS. 3A-3D illustrate an orthodontic force module assembly 300 that includes an orthodontic force module 302 and a pin connector 304 positioned at or near an end of orthodontic force module 302 use in attaching orthodontic force module 302 to an orthodontic buccal tube 306. FIG. 3A illustrates orthodontic force module assembly 300 before being attached to buccal tube 306. By way of example, pin connector 304 includes an elongate pin body 310 configured for insertion through a tunnel 312 in buccal tube 306 (as illustrated in FIG. 3B) and a flange 314 used to provide a pivot connection between pin connector 304 and an end 316 of force module 302. The pivoting aspect of pin connector 304 permits rotational movement of force module 302 relative to buccal tube 306 during use.

Figure 3C:
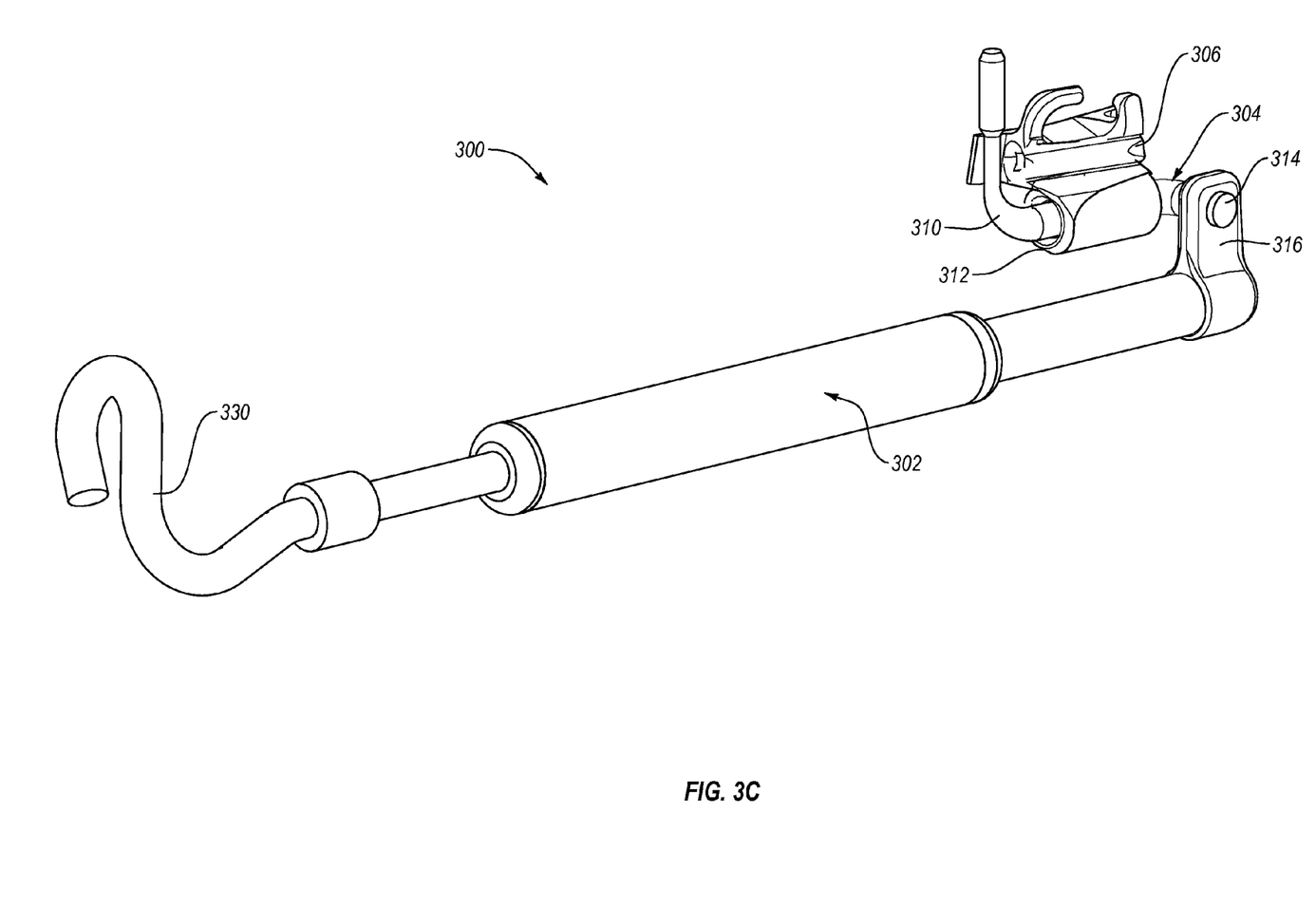
FIG. 3C illustrates a pin connector being used to attach an orthodontic force module to an orthodontic buccal tube as in FIG. 3B, showing an intermediate configuration in which the pin connector has been bent 90°.
Figure 3D:
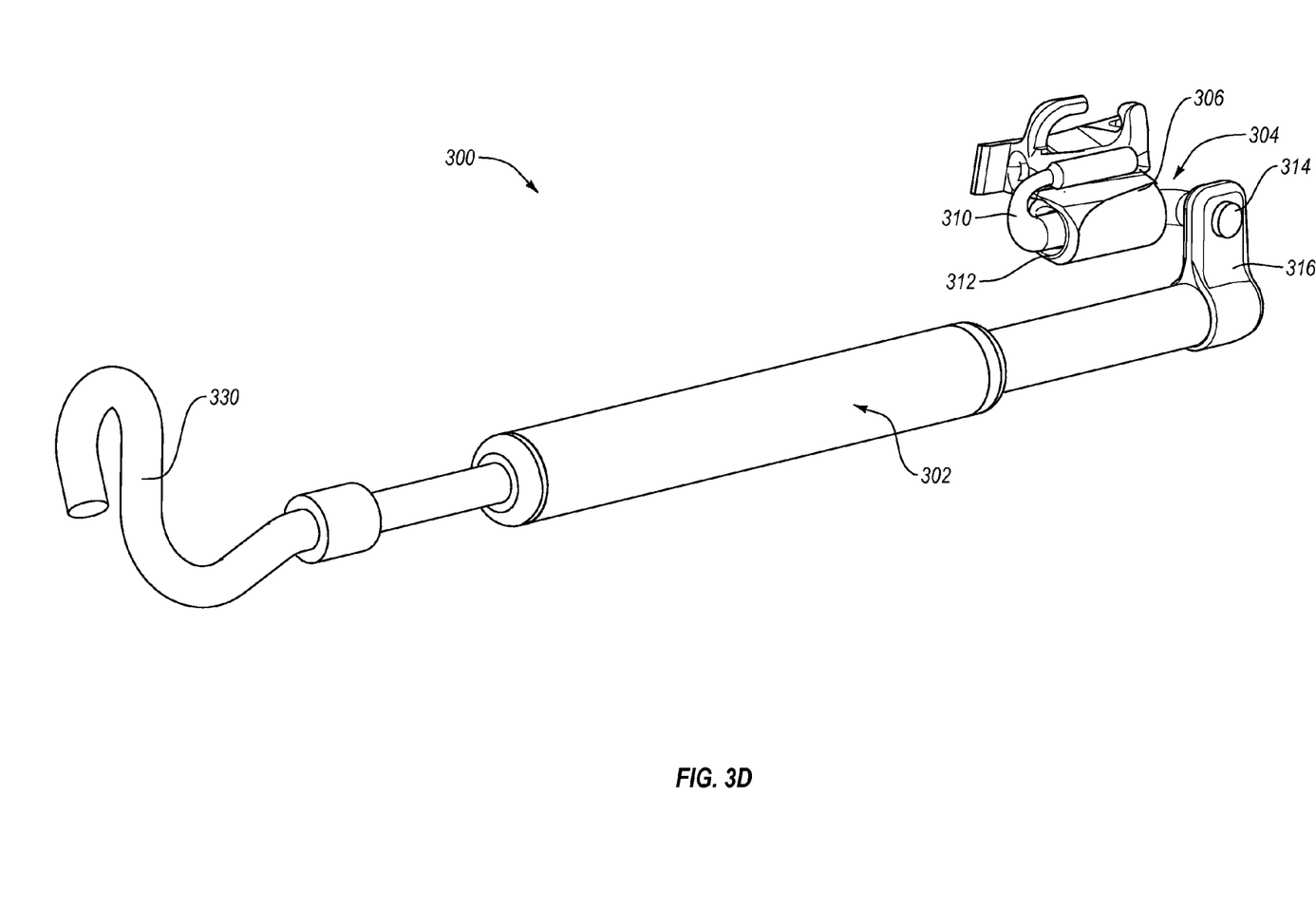
FIG. 3D illustrates a pin connector being used to attach an orthodontic force module to an orthodontic buccal tube as in FIG. 3B, showing a final configuration in which the pin connector has been bent 180° to secure an end of the force module to the buccal tube.

Elongate pin body 310 includes a region of reduced cross-sectional diameter provided by first, second and third pin body segments 320, 322, 324, respectively. In this embodiment, second pin body segment 322 includes a sub-region of gradually reducing diameter in order to provide for controlled bending of pin body 310 in the region of second pin body segment 322. FIG. 3C illustrates an intermediate configuration in which pin connector 304 has been preferentially bent 90° at a desired location. FIG. 3D illustrates a final configuration in which pin connector 304 has been bent 180° in order to secure end 316 of force module 302 to buccal tube 306. Force module 302 may also include a hook 330 (or recess, not shown) that provides means for attaching force module 302 to an orthodontic archwire or other orthodontic appliance.

The pin connectors of the present invention may be formed from any suitable material(s) that can be bent and then maintain the bend. Examples of deformable materials include one or more metals or allows and/or polymers. According to one embodiment, at least the elongate pin body of the pin connector can be made from stainless steel (e.g., 316L) or other biocompatible metal or alloy. According to another embodiment, at the non-bending components of the pin connector may include a molded polymer material.

The pin connector may be manufactured using any appropriate molding and/or machining process known in the art and that is suitable for the particular material being acted upon. For example, the pin connector can be made by machining, casting, injection molding, metal injection molding (MIM), additive manufacturing processes, drawing and the like. Machining at least the region of reduced cross-sectional diameter may be advantageous to provide a high degree of accuracy of the cross-sectional diameter.

According to several embodiments, pin connectors are provided which can have an elongate pin body with a length and a region of reduced cross-sectional diameter positioned along the elongate pin body in order for the pin connector to preferentially bend in such a way as to provide a predetermined amount of play between a force module and an orthodontic buccal tube. According to one embodiment, pin connectors can be designed to provide a predetermined amount of play between a force module and an orthodontic buccal tube that is preferably in a range of about 1.5 mm to about 2.5 mm, more preferably in a range of about 1.75 mm to about 2.25 mm, and most preferably about 2 mm.

In order to provide a desired amount of play between a force module and an orthodontic buccal tube, pin connectors can include a first pin body segment having a length in a range of about 2.5 mm to about 5 mm, a second pin body segment having a length in a range of about 4 mm to about 7 mm, and a third pin body segment having a length in a range of about 2 mm to about 4 mm.

In order to provide a desired amount of preferential bend in a region of reduced cross-sectional diameter, pin connectors can include a first pin body segment having a cross-sectional diameter in a range of about 0.5 mm to about 1.5 mm, a second pin body segment having a cross-sectional diameter in a range of about 0.25 mm to about 1 mm, and a third pin body segment having a cross-sectional diameter in a range of about 0.5 mm to about 1.5 mm. In this way, pin connectors can be provided in which the second pin body segment has a cross-sectional diameter that about 25% to about 90% of the cross-sectional diameters of the first and third pin body segments.

Pin connectors can include first, second and third pin body segments which are configured so as to prevent significant bending of the elongate pin body in the first and third pin body segments when attaching the pin connector to an orthodontic buccal tube or other orthodontic appliance.

According to another aspect of the invention orthodontic force module assemblies for correcting Class II and/or Class III malocclusions are provided, which include an orthodontic force module and a pin connector. The orthodontic force module can have a proximal end and a distal end, and the pin connector may extend from the distal end of the orthodontic force module. The pin connector includes an elongate pin body which extends between a proximal end and a distal end and includes a region of reduced cross-sectional diameter that causes the elongate pin body to preferentially bend in the region of reduced cross-sectional diameter and not in one or more adjacent regions when attaching the pin connector to an orthodontic buccal tube or other orthodontic appliance. The pin connector further includes an extension rod interconnecting the proximal end of the pin body to the distal end of the orthodontic force module. The orthodontic force module assembly may further comprise proximal attachment means (e.g., a hook) at the proximal end of the orthodontic force module assembly for attachment to an arch wire and/or a bracket.

A method of attaching an orthodontic force module to an orthodontic buccal tube or other orthodontic appliance comprises: (1) providing an orthodontic force module with a pin connector at an end thereof; (2) inserting an elongate pin body of the pin connector into a tunnel of the orthodontic buccal tube or other orthodontic appliance; and (3) bending a portion of the elongate pin body in order to secure the pin connector to the orthodontic buccal tube or other orthodontic appliance, (4) the elongate pin body preferentially bending in a predetermined region as a result of the predetermined region having a reduced cross-sectional diameter compared to a cross-sectional diameter of at least one adjacent region. According to one embodiment, bending the elongate pin body in the predetermined region provides play between the orthodontic force module and the orthodontic buccal tube or other orthodontic appliance that is preferably in a range of about 1.5 mm to about 2.5 mm, more preferably in a range of about 1.75 mm to about 2.25 mm, and most preferably about 2 mm.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A pin connector for use in attaching an orthodontic force module to an orthodontic buccal tube or other orthodontic appliance and configured to bend in a predetermined region, comprising:
an elongate pin body initially extending substantially along a main axis between a proximal end and a distal end and being comprised of:
a first pin body segment initially extending substantially along the main axis from the proximal end of the pin body to a first location on the pin body between the proximal and distal ends;
a second pin body segment initially extending substantially along the main axis distally from the first location to a second location on the pin body between the first location and the distal end; and
a third pin body segment initially extending substantially along the main axis distally from the second location to the distal end of the pin body,
the second pin body segment having an average cross-sectional diameter that is less than a cross-sectional diameter of at least a portion of the first pin body segment and that is less than a cross-sectional diameter of at least a portion of the third pin body segment; and
an extension rod rigidly attached to and extending laterally from the proximal end of the elongate pin body at an angle transverse to the main axis, wherein the extension rod is configured for attachment to an end of an orthodontic force module.

2. A pin connector as in claim 1, wherein the elongate pin body and extension rod are integrally formed as a single piece of deformable material.

3. A pin connector as in claim 2, wherein the deformable material comprises metal.

4. A pin connector as in claim 1, wherein the elongate pin body is initially substantially straight, and wherein the second pin body segment has a length and/or bendability so as to preferentially bend near the first location on the pin body when initially bending the elongate pin body and then preferentially bend near the second location on the pin body when completing the bending of the elongate pin body.

5. A pin connector as in claim 4, wherein the second pin body segment is configured to preferentially bend near the first location on the pin body during a first 90° of bending then preferentially bend near the second location on the pin during a second 90° of bending.

6. A pin connector as in claim 1, wherein the first pin body segment has a length in a range of about 2.5 mm to about 5 mm, wherein the second pin body segment has a length in a range of about 4 to about 7 mm, and wherein the third pin body segment has a length in a range of about 2 mm to about 4 mm.

7. A pin connector as in claim 1, wherein the first pin body segment has a cross-sectional diameter in a range of about 0.5 mm to about 1.5 mm, wherein the second pin body segment has a cross-sectional diameter in a range of about 0.25 mm to about 1 mm, and wherein the third pin body segment has a cross-sectional diameter in a range of about 0.5 mm to about 1.5 mm.

8. A pin connector as in claim 1, wherein the average cross-sectional diameter of the second pin body segment is about 25% to about 75% of the cross-sectional diameters of the at least a portion of the first and the third pin body segments.

9. A pin connector as in claim 1, wherein the region of reduced cross-sectional diameter causes the elongate pin body to preferentially bend in the second pin body segment and not in the first and third pin body segments when attaching the pin connector to an orthodontic buccal tube or other orthodontic appliance.

10. A pin connector as in claim 1, wherein the elongate pin body has a length and the region of reduced cross-sectional diameter is positioned along the elongate pin body in order for the pin connector to provide play between the force module and orthodontic buccal tube or other orthodontic appliance when attached thereto in a range of about 1.5 mm to about 2.5 mm.

11. A pin connector as in claim 1, wherein the elongate pin body has a length and the region of reduced cross-sectional diameter is positioned along the elongate pin body in order for the pin connector to provide play between the force module and orthodontic buccal tube or other orthodontic appliance when attached thereto in a range of about 1.75 mm to about 2.25 mm.

12. A pin connector as in claim 1, wherein the elongate pin body has a length and the region of reduced cross-sectional diameter is positioned along the elongate pin body in order for the pin connector to provide about 2 mm of play between the force module and orthodontic buccal tube or other orthodontic appliance when attached thereto.

13. A pin connector as in claim 1, wherein the second pin body segment provides a gradually reducing cross-sectional diameter.

14. A pin connector as in claim 1, wherein the second pin body segment has a constant cross-sectional diameter from the first location to the second location.

15. An orthodontic force module assembly for correcting Class II and/or Class III malocclusions, comprising:
an orthodontic force module having a proximal end and a distal end and attachment means at the proximal end of the orthodontic force module assembly for attachment to an arch wire and/or a bracket; and
a pin connector extending from the distal end of the orthodontic force module and configured for attachment of the orthodontic force module to an orthodontic buccal tube or other orthodontic appliance, the pin connector being comprised of:
an elongate pin body extending between a proximal end and a distal end and having a region of reduced cross-sectional diameter disposed between the proximal end and the distal end, the region of reduced cross-sectional diameter being reduced in diameter compared to a cross-sectional diameter of at least a region of the pin body distal to the region of reduced cross-sectional diameter; and
an extension rod interconnecting the proximal end of the pin body to the distal end of the orthodontic force module.

16. An orthodontic force module assembly as in claim 15, the elongate pin body of the pin connector being comprised of a plurality of segments including:
a first pin body segment extending from the proximal end of the pin body to a first location on the pin body between the proximal and distal ends;
a second pin body segment extending distally from the first location to a second location on the pin body between the first location and the distal end; and
a third pin body segment extending distally from the second location to the distal end of the pin body,
the second pin body segment providing the region of reduced cross-sectional diameter,
the second pin body segment having an average cross-sectional diameter that is less than a cross-sectional diameter of at least a portion of the first pin body segment and less than a cross-sectional diameter of at least a portion of the third pin body segment.

17. An orthodontic force module assembly as in claim 15, wherein the proximal attachment means comprises a hook.

18. An orthodontic force module assembly as in claim 16, wherein the second pin body segment provides a gradually reducing cross-sectional diameter.

19. An orthodontic force module assembly as in claim 16, wherein the second pin body segment has a constant cross-sectional diameter from the first location to the second location.

20. An orthodontic force module assembly as in claim 16, wherein the region of reduced cross-sectional diameter causes the elongate pin body to preferentially bend in the second pin body segment and not in the first and third pin body segments when attaching the pin connector to an orthodontic buccal tube or other orthodontic appliance.

21. A method of attaching an orthodontic force module to an orthodontic buccal tube or other orthodontic appliance, comprising:
    providing an orthodontic force module with a pin connector at an end thereof, the pin connector being comprised of a plurality of segments including:
        a first pin body segment extending from the proximal end of the pin body to a first location on the pin body between the proximal and distal ends;
        a second pin body segment extending distally from the first location to a second location on the pin body between the first location and the distal end; and
        a third pin body segment extending distally from the second location to the distal end of the pin body,
        the second pin body segment having an average cross-sectional diameter that is less than a cross-sectional diameter of at least a portion of the first pin body segment and less than a cross-sectional diameter of at least a portion of the third pin body segment;
    inserting an elongate pin body of the pin connector into a tunnel of the orthodontic buccal tube or other orthodontic appliance; and
    bending a portion of the elongate pin body in order to secure the pin connector to the orthodontic buccal tube or other orthodontic appliance,
    the elongate pin body preferentially bending in a predetermined region as a result of the predetermined region having a reduced cross-sectional diameter compared to a cross-sectional diameter of at least a region of the elongate pin body distal to the predetermined region.

22. A method as in claim 21, wherein bending the elongate pin body in the predetermined region provides play between the orthodontic force module and the orthodontic buccal tube or other orthodontic appliance in a range of about 1.5 mm to about 2.5 mm.

23. A method as in claim 21, wherein bending the elongate pin body in the predetermined region provides play between the orthodontic force module and the orthodontic buccal tube or other orthodontic appliance in a range of about 1.75 mm to about 2.25 mm.

24. A method as in claim 21, wherein bending the elongate pin body in the predetermined region provides play between the orthodontic force module and the orthodontic buccal tube or other orthodontic appliance of about 2 mm.

25. A pin connector for use in attaching an orthodontic force module to an orthodontic buccal tube or other orthodontic appliance and configured to bend in a predetermined region, comprising:
    an elongate pin body extending between a proximal end and a distal end and being comprised of:
        a first pin body segment extending from the proximal end of the pin body to a first location on the pin body between the proximal and distal ends;
        a second pin body segment extending distally from the first location to a second location on the pin body between the first location and the distal end; and
        a third pin body segment extending distally from the second location to the distal end of the pin body,
        the second pin body segment providing a gradually reducing cross-sectional diameter and having an average cross-sectional diameter that is less than a cross-sectional diameter of at least a portion of the first pin body segment and that is less than a cross-sectional diameter of at least a portion of the third pin body segment; and
    an extension rod rigidly attached to and extending laterally from the proximal end of the elongate pin body and configured for attachment to an end of an orthodontic force module.

26. A pin connector as in claim 25, wherein the elongate pin body is initially substantially straight.

27. An orthodontic force module assembly for correcting Class II and/or Class III malocclusions, comprising:
    an orthodontic force module having a proximal end and a distal end; and
    a pin connector extending from the distal end of the orthodontic force module and configured for attachment of the orthodontic force module to an orthodontic buccal tube or other orthodontic appliance, the pin connector being comprised of:
    an elongate pin body extending between a proximal end and a distal end and being comprised of:
        a first pin body segment extending from the proximal end of the pin body to a first location on the pin body between the proximal and distal ends;
        a second pin body segment extending distally from the first location to a second location on the pin body between the first location and the distal end; and
        a third pin body segment extending distally from the second location to the distal end of the pin body,
        the second pin body segment providing a gradually reducing cross-sectional diameter and having an average cross-sectional diameter that is less than a cross-sectional diameter of at least a portion of the first pin body segment and that is less than a cross-sectional diameter of at least a portion of the third pin body segment; and
    an extension rod rigidly attached to and extending laterally from the proximal end of the elongate pin body and configured for attachment to an end of an orthodontic force module.

* * * * *